United States Patent [19]

Hill

[11] 4,058,621

[45] Nov. 15, 1977

[54] IRON COMPLEXES AND FOODSTUFFS CONTAINING THEM

[75] Inventor: William W. Hill, St. Paul, Minn.

[73] Assignee: Peter, Strong & Company, Inc., Port Chester, N.Y.

[21] Appl. No.: 630,437

[22] Filed: Nov. 10, 1975

Related U.S. Application Data

[63] Continuation-in-part of Ser. No. 552,541, Feb. 24, 1975, abandoned, and Ser. No. 565,811, March 31, 1975, abandoned, each is a continuation of Ser. No. 455,873, March 28, 1974, abandoned, which is a continuation of Ser. No. 417,553, Nov. 20, 1973, Pat. No. 3,901,874, Continuation-in-part of Ser. No. 342,393, March 19, 1973, abandoned, which is a continuation of Ser. No. 260,521, June 7, 1972, abandoned, which is a continuation of Ser. No. 39,601, May 22, 1970, abandoned.

[51] Int. Cl.$^2$ ............................................. A01N 9/00
[52] U.S. Cl. ...................................... 424/295; 426/3; 426/592; 426/648; 426/656; 426/658; 536/2
[58] Field of Search .................... 426/3, 74, 592, 656, 426/658, 648; 424/147, 180, 295, 48, 177; 260/209 R, 209.5; 252/313, 430; 536/2, 3

[56] References Cited

U.S. PATENT DOCUMENTS

| | | | |
|---|---|---|---|
| 2,338,534 | 1/1944 | Pasternack et al. | 260/209.5 |
| 3,035,985 | 5/1962 | Stoyle et al. | 424/295 |
| 3,076,747 | 2/1963 | Hallberg | 424/295 |
| 3,208,995 | 9/1965 | Dodd et al. | 536/3 |
| 3,734,742 | 5/1973 | Morse et al. | 424/295 |
| 3,821,192 | 6/1974 | Montgomery et al. | 260/209 R |
| 3,901,874 | 8/1975 | Hill | 536/3 |

FOREIGN PATENT DOCUMENTS 514,504  4/1930  Germany

OTHER PUBLICATIONS

Fretz et al., "Biological Availability in Animals of Iron from Common Dietary Sources," J. Agr. Food Chem. 18, No. 4, 1970, pp. 647–651.

*Primary Examiner*—R. B. Penland
*Attorney, Agent, or Firm*—Thomas M. Meshbesher

[57] ABSTRACT

A six-carbon uronate (e.g. galacturonate or glucuronate) moiety is capable of complexing up to about 3 gram atoms of iron to provide a hematinic compound with high iron content, high bioavailability of iron (up to about 100% of FeSO$_4$), reduced side effects (e.g. little or no metallic taste), and excellent compatibility with foodstuffs, pharmaceutical extenders, etc.

10 Claims, No Drawings

IRON COMPLEXES AND FOODSTUFFS CONTAINING THEM

CROSS REFERENCE TO RELATED APPLICATIONS

This application is a continuation-in-part of my copending applications Ser. No. 552,541, filed Feb. 24, 1975 now abandoned and Ser. No. 565,811, filed Mar. 31, 1975, now abandoned which in turn were continuations of my application Ser. No. 455,873, filed Mar. 28, 1974, now abandoned which in turn was a continuation of my application Ser. No. 417,553, filed Nov. 20, 1973, now U.S. Pat. No. 3,901,874, issued Aug. 26, 1975, and said Ser. No. 417,553 is a continuation-in-part of my Ser. No. 342,393, filed Mar. 19, 1973, now abandoned, which is a continuation of Ser. No. 260,521, filed June 7, 1972, now abandoned, which is a continuation of Ser. No. 39,601, filed May 22, 1970, which is now abandoned. In addition to the foregoing cited applications, Ser. Nos. 260,801 and 260,520 were divided out of said Ser. No. 39,601 and are now abandoned.

My application Ser. No. 417,553, filed Nov. 20, 1973, now U.S. Pat. No. 3,901,874, issued Aug. 26, 1975, and all divisional or continuing applications related thereto, contains a disclosure regarding hydrolysis of pectin and other uronic moiety gums and use of the hydrolyzates in complexing iron.

FIELD OF THE INVENTION

This invention relates generally to iron-containing compounds of the type often referred to in the medical and biological sciences as "hematinics". An aspect of this invention relates to the reaction product of a uronic acid (or the lactone form thereof or the neutralized, i.e., carboxylate form thereof) and a water soluble iron salt. Another aspect of this invention relates to a solid, iron-containing compound which has a high level of bioavailable iron, when tested according to the cyanomethemoglobin method of Drabkin for hemoglobin determination. Still another aspect of this invention relates to hematinic compounds or complexes in pharmaceutically acceptable extending media or as additives to foodstuffs. Still another aspect of this invention relates to an iron complex or compound containing in excess of 20 weight percent iron, which iron is in a substantially bioavailable form.

DESCRIPTION OF THE PRIOR ART

It is well known that mammals require iron in their diets. Although the amount of iron required by a mammal is not large, in comparison, say, to protein requirements, the ingestion of iron appears to be essential to the maintenance of a high level of hemoglobin in the blood. Iron deficiency anemia can occur naturally and has been experimentally induced or created in a wide variety of mammalina species, including the typical experimental animals such as rodents. The occurrence of iron deficiency anemia in humans, of course, is well established.

Although there are foods which are rich in iron, some of the mainstays of a mammalian diet, e.g. milk, are relatively low in iron. For this and other reasons, it is a fairly common practice to fortify some foods and animal feed materials with bio-available iron-containing compounds (generally referred to as hematinics). The use of hematinic additives in foods can reverse or prevent iron deficiency anemia. In severe cases of anemia, parenteral routes of administration (e.g. intramuscular injection) have been used to increase body stores of iron and hence improve hemoglobin levels. Generally speaking, however, the commonest use of hematinic compounds relates to the oral ingestion route, either as iron tablets or additives to foodstuffs. Mammals can tolerate fairly high dosage levels by the oral route. For example, the $LD_{50}$ for oral ingestion of ferrous sulfate in rats is 5,000 milligrams per kilogram of body weight. By the intravenous route, the $LD_{50}$ for rabbits is 99 milligrams per kilogram of body weight. It has been found that humans can tolerate oral dosages of about 300 milligrams of ferrous sulfate, but not without risk of some serious side effects such as gastro-intestinal disturbances. Whatever the problems of oral hematinic administration, however, it is a simple fact that this type of administration is practiced on a grand scale with respect to a variety of foodstuffs including cereals, animal feeds, pet food, etc.

The problems connected with the use of ferrous sulfate as a hematinic can be particularly acute under certain circumstances. In addition to the side effects (gastro-intestinal disturbances, hepatic damage, discoloration of feces, etc.) this compound can discolor flour, cereal and other foodstuffs. Furthermore, its somewhat metallic taste may be unpalatable to both animals and humans; its tendency to produce rancidity in some foodstuffs, its incompatibility with a wide variety of materials (e.g. alkalies, tartrates, tannins, vegetable astringents, etc.), and its susceptibility to oxidation are other potential (and sometimes very real) disadvantages. The outstanding advantages of ferrous sulfate as a source of iron for humans, livestock, etc., are its relatively low cost and its extremely high bioavailability. Indeed, ferrous sulfate is generally accepted as the standard for bioavailability, and a hematinic compound with the same bioavailability as ferrous sulfate would be regarded as providing substantially 100% bioavailable iron.

Many alternatives to ferrous sulfate have been discovered, and, of these, some have been accepted for medical and/or veterinary use. For example, ferrous gluconate can be administered to humans orally in 300 mg. doses. Side effects may be similar to ferrous sulfate, however. Many other iron salts with adequate hematinic properties could be mentioned. For the most part, these iron salts contain anions or other moieties which were obtained by a chemical synthesis or an expensive isolation and purification process. It has been suggested that iron can be complexed with alginates or pectin for hematinic use, but, again, chemical procedures for producing the drug can be complicated or expensive. Furthermore, it does not appear that detailed bioavailability data is presently available regarding such alginates and pectinates, and total iron content can, in any event, be far below $FeSO_4$.

With respect to iron-containing derivatives of alginic acid, see U.S. Pat. No. 3,208,995 (Dodd et al), issued Sept. 28, 1965. For disclosure relating to an iron-pectin complex, see U.S. Pat. No. 3,324,109 (Eichel), issued June 6, 1967.

It is known that hexoses and derivatives thereof, including acids of the formula $HOOC(CHOH)_4CH_2OH$ (e.g. gluconic acid) are capable of complexing iron to form useful medicaments. See Deutsches Reichspatent (D.R.P.) 514,504 (Schmidt et al), of Dec. 13, 1930. Schmidt et al report $C_6H_8O_7Na\ Fe\cdot xH_2O$ as the empirical formula of the complex. See also:

Ber. Deut. Chem., 65, pp. 187–190 and 190–191 (1932);
Ber. Deut. Chem., 66, 1545–1556 (1933);
and U.S. Pat. No. 1,786,490 (Huff et al), issued Dec. 30, 1930.

SUMMARY OF THE INVENTION

It has now been found that substantially monomeric six-carbon uronic acids (e.g. galacturonic acid, which can be obtained inexpensively from the acid-hydrolysis of naturally-occurring polygalacturonic acid) have a surprising ability to complex and/or react with extremely large amounts of iron to provide unusually potent hematinic compounds, wherein the bioavailability of the iron is substantially 100% of that of ferrous sulfate, and wherein the side effects of some iron compounds (e.g. darkening of feces) are minimized. Although this invention is not bound by any theory, it is presently believed that the aldehyde functional group (-CHO) of the uronic moiety is somewhat more compatible with the physiology of mammals than other common functional groups such as methylol (-CH$_2$OH). The six-carbon uronic acids (e.g. galacturonic acid, mannuronic acid, and glucuronic acid) have the formula C$_6$H$_{10}$O$_7$ and can be represented either as cyclic Haworth formulas or as free aldehyde-containing structures, i.e.

(COOH)(CHOH)$_4$CHO

In accordance with the principles of this invention, expensive enzymatic hydrolyses of pectin are unnecessary. A simple, brute force treatment of the pectin with mineral acids or strong organic acids is very workable, since the monomeric form of the uronic acid (particularly a monomer converted to carboxylate form by neutralization with a strong base) is a fully operative means for complexing a large amount of bioavailable iron; indeed, the monomeric uronate presently appears to be preferred. Monomeric uronic acid lactones (e.g. deltalactones) are also operative.

DETAILED DESCRIPTION

The compounds to be described can provide several desiderata of the art of hematinics. For example, the iron in these complexes is so completely complexed that there are not enough iron cations available to be precipitated out as iron carbonate or iron hydroxide even in strongly alkaline solution. Several benefits are believed to flow from this stable complexing. For one thing, the taste of these compounds in aqueous solution is agreeably fruit-like in nature and generally devoid of the disagreeable metallic character generally associated with some soluble iron compounds. Furthermore, the chemical stability and storage life of the complexes (e.g. resistance to oxidation or reduction) appears to be excellent.

Although glucuronic acid is often synthesized from glucose rather than isolated from natural sources, the natural occurrence of galacturonic acid, in polymeric form, is very wide-spread and the acid can be recovered in pure form from its natural sources. Polygalacturonic acid appears, for example, as part of the molecules of plant hydrocolloids such as pectin. Thus, polygalacturonic acid is a constituent of many human and animal foodstuffs, especially fruits such as apples and citrus fruits. Galacturonic acid, in short, can be considered to be a component part or a close relative of materials already naturally occurring in foodstuffs (including animal feeds), and can further be considered to be very compatible with mammalian physiology.

As mentioned previously, the presence of the aldehyde group in the preferred six-carbon uronic acids is presently believed to be a factor in the outstanding bioavailability and/or biocompatability of the iron complexes of this invention; stated another way, the similarity in structure between a C$_6$ uronic acid moiety and an aldohexose such as galactose, mannose, glucose, etc. appears to be significant. Another related explanation apparently supported in the literture (e.g. *Annals of the N.Y. Academy of Sciences*, 94, Article 1, pp. 44–54 and 297–307 (1961) is that aldohexoses and uronic acids can be utilized directly in the synthesis of mucopolysaccharides.

In the familiar Haworth structures, the aldehyde group contributes the ring oxygen atom and the ring carbon on which the carboxyl (COOH) is substituted. In other words, the aldehyde group can participate in cyclization to an analog of the glycoside (e.g. pyranoside) structure of an aldohexose. According to the literature on aldohexoses, the glycoside structures (alpha and beta) are in equilibrium with the aldehydic form.

As is known in the art, the Haworth structural formula for the naturally occurring (D) isomer of galacturonic acid is as follows:

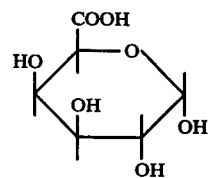

The Haworth structural formula for beta-D-glucuronic acid is as follows:

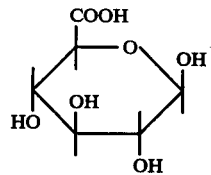

As in the case of analogous carbohydrates, the D-form is generally the most compatible with the physiology of mammals. Furthermore, the D-forms can occur in nature, obviating the need for resolution of optical isomers. Racemates or racemic mixtures can be operative in this invention, but there is no reason to prefer such mixtures over the naturally occurring D-forms.

Regardless of whether the six-carbon uronic acid is in the aldehydic or pyranoside form, the formula of the iron complex itself can be represented as:

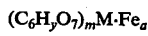

(C$_6$H$_y$O$_7$)$_m$M·Fe$_a$ wherein M is a pharmaceutically acceptable cation; $m$ is the valence of M (e.g. a number ranging from 1 to 6, more typically an integer ranging from 1 to 3 or 1 to 4); $y$ is an integer ranging from 5 to 9; and $a$ is a small multiple of $m$, ordinarily a multiple (including fractional numbers) ranging from about $m$ to about $3m$. Thus, when M is Na and $m$ is one, $a$ can range from about 1 to about 3. These results generally agree with the findings of Schmidt et al. (D.R.P. 514,504), wherein the formula $C_6H_8O_7NaFe$ (in hydrated form) was reported for the reaction products of sodium gluconate ($NaC_6H_{11}O_7$) and iron acetate or iron chloride; $C_6H_6O_8KNaFe$ was reported for the ferrous complex of the Na-K salt of saccharic acid; $C_6H_5O_8KNaFe$ for the ferric complex of the Na-K salt of saccharic acid; and $(C_6H_4O_8Na_2)_3Fe_4$ for a higher ferric complex of the sodium salt of mucic acid, all of the foregoing also being hydrates. Thus, Schmidt et al appear to suggest that the number of H atoms in the gluconate or saccharate or mucate complex (exclusive of hydrogen in water of hydration) is found by subtracting the valence of iron (e.g. 11-3=8 for gluconate), which further suggests complexing of iron through the OH radicals of the -(CHOH)$_4$- "spine" of the hexoic moiety rather than through the carboxylate anion.

Stated another way, the hematinics of this invention have been found, by elemental analysis, to contain at least about one gram-atom of iron per uronate moiety. Elemental analysis is, however, complicated by the likelihood that simple metal salts such as sodium chloride can contaminate the hematinic and the possibility that some iron cations could be associated with the complex in other ways. Based upon the surprising effectiveness of the uronates in complexing iron, the percent by weight of iron in compounds of this invention should theoretically range from about 20% to about 40%, and elemental analysis shows iron contents in this range most commonly in excess of 25 weight-%. The simple salts result from neutralization reactions carried out during the synthesis of the complex, which reactions will be discussed in detail subsequently.

In a preferred embodiment of this invention, essentially monomeric galacturonic acid, in neutralized (galacturonate) form, complexes a water soluble iron salt (e.g. ferric chloride) in an acid medium. When the acid medium and the galacturonic acid are neutralized with sodium hydroxide or alkaline sodium salt (e.g. sodium carbonate), the resulting complex contains about 25-34% (e.g. 29-30%) by weight of iron and about 7-9% by weight of sodium, depending upon the limits of experimental error in the analysis, the amount of sodium chloride contaminant, and the like. This preferred embodiment of the invention, when tested according to the cyanomethemoglobin method of Drabkin for hemoglobin determination compares very favorably to ferrous sulfate (the accepted standard). Test data indicates substantially 100% of the iron bioavailability of ferrous sulfate in a curative test, and at least 64% in a prophylactic test. The "curative" test results can be obtained in an oral administration technique, wherein the test animals are fed a prescribed iron-poor diet and are brought to an anemic condition through a controlled experimental technique. The iron complex administered to the experimental group of animals results in improvement in hemoglobin levels which are quantitively determined by the Drabkin method, and no such hemoglobin improvement is observed in the "negative control" group, which is given no hematinic. This test technique is generally standardized and has been used, with many variations, to determine bioavailability of iron in a variety of hematinics. The variations in the "curative" test method are not believed to be significant, insofar as this invention is concerned. In any event, long-standing experience with this type of hemoglobin determination has generally led to the acceptance of ferrous sulfate as a standard for bioavailability of iron.* For this reason alone, the test results obtained with complexes of this invention are believed to be surprising. The test data suggests that the preferred embodiment of this invention may even exceed the standard in bioavailability. In an art in which attainment of a substantial fraction of the potency (i.e., bioavailability) of the standard indicates good performance, a rating of "as good or better than" the standard can be a step forward in the art. Furthermore, this high performance is attained along with other improvements, e.g. improved taste.

*See Fritz et al, JAOAC, 55: 1128 (1972); Pla et al, JAOAC, 54: 13 (1971); Fritz et al, J. Agr. Food Chem., 18: 647 (1970).

The preferred iron complexes of this invention are generally water soluble, dark brown solids. These solids are sparingly soluble, at best, in lower alkanols and other watermiscible polar organic solvents. Accordingly, as will be explained subsequently, the solids can be precipitated from aqueous solutions with 50-99% aqueous solutions of $C_1$-$C_3$ alkanols, the preferred alkanol being 2-propanol (isopropyl alcohol). In some instances, precipitation with an alcohol may lead to the formation of a viscous, dark-colored oil, but redissolving and reprecipitation of the complex can be used to recover solid crystals.

Based upon quantitively-controlled synetheses and elemental analyses, it has been concluded that preferred embodiments of this invention consist essentially of the galacturonic acid derivatives having the formulas $C_6H_6O_7Na\cdot Fe$ and $C_6H_6O_7Na\cdot Fe_2$, which can be contaminated by by-products such as soluble sodium salts of pharmaceutically acceptable anions (e.g. chloride). As noted previously, it is not necessary to remove the biologically acceptable by-products or to isolate the iron complex in analytical reagent grade purity. Nor is it necessary, at any stage in the process of making complexes of this invention, to totally remove low molecular weight polymers of the uronic acid (e.g. dimers, trimers, etc.). Of course, from a quality control standpoint, it is convenient (but not necessary) to use a chemically pure six-carbon D-uronic acid as a starting material, thereby obtaining a strictly monomeric product. Since at least incidental amounts of dimers and trimers of the uronic acid can be tolerated, the term "essentially monomeric" or "substantially monomeric" is used in this application to describe the carboxylic or carboxylate starting material used in this invention.

OBTAINING THE URONIC ACID OR URONATE STARTING MATERIAL

As mentioned previously, D-glucuronic acid can be produced synthetically. This uronic acid is also widely distributed in the plant and animal kingdom and may appear in urine as a metabolite. Synthesis from glucose presently appears to be the most economical method for producing this compound.

Galacturonic acid can be obtained as a D-isomer from the naturally occurring polymeric form by enzymatic or acid hydrolysis. From an industrial availability standpoint, acid hydrolyzates are particularly attractive. Plentiful sources of pectin or protopectin are already being commercially hydrolyzed with sulfur dioxide or hydrochloric acid to so-called food grade or jelly grade pectin. The food grade pectin is relatively insoluble in aqueous media containing lower alkanols, aluminum salts, and a variety of other precipitating agents. However, substantially monomeric galacturonic acid can be recovered from the supernatent medium with a minimum of complications.

In the pectin recovery art, hydrolysis conditions are normally controlled quite carefully to avoid undue degradation of the pectin which is to be precipitated from solution. This careful control is almost entirely incidental or even irrelevant to the purposes of this invention. Thus, an off-stream of hydrolyzate or of pectin-containing raw materials can be treated with "brute force" (relatively speaking) to provide the substantially monomeric hydrolyzate, which is the preferred starting material for complexes of this invention. Furthermore, since incidental amounts of dimers, trimers, and other low molecular weight pectin fragments can be tolerated, there is no need to isolate chemically pure galacturonic acid for synthesis of the desired iron complex. Stated another way, a very crude monomeric acid can be "harvested" from virtually any suitable off-stream in a commercial process of pectin manufacture, or even from pectin-containing vegetable matter (e.g. sugar beet waste) subjected to prolonged storage. The crude galacturonic acid or galacturonate salt can, for the sake of convenience be recovered in solid form by known precipitation techniques. Among such techniques is the neutralization of the carboxyl group of the acid with a combination of sodium hydroxide, potassium hydroxide, and calcium oxide and/or strontium oxide or hydroxide (or basic salts of sodium, calcium, or strontium) to produce double salts of galacturonic acid which are known to be substantially insoluble in water, salts, which can be used directly as starting materials in making the hematinics of this invention: see U.S. Pat. No. 2,338,534. The crude acid product can also be recovered by evaporation. Furthermore, it has been found that galacturonic acid can complex a variety of metals such as Ca, Co, Ni, Mn, Cu, and Zn.

In the context of this invention, it is the neutralized (galacturonate) form of the acid which is preferred for complexing of iron, since a hematinic bioavailable iron content in excess of 20 wt. % or even 25 wt. % can be provided in this manner. Any suitable bases which provide pharmaceutically acceptable cations can be used for neutralization, provided that these bases are strong enough (e.. have a $pK_a$ in excess of 8 or 9). The preferred strong bases are sodium and potassium hydroxide or basic salts of sodium or potassium. Such basic salts include salts of NaOH or KOH with pharmaceutically acceptable anions of relatively weak acids such as carbonic acid. Thus, there are substantially no difficulties encountered in the neutralization of galacturonic acid with soda ash (sodium carbonate), provided that the resulting carbon dioxide is driven out of or released from the solution, e.g. by gentle heating. In any event, neutralization of the galacturonic acid with strong bases is generally spontaneous at room temperature and requires no special processing steps other than stirring or other agitation of the reactants in aqueous solution. As mentioned previously, uronic acid lactones (e.g. delta-lactones) can be used in the synthesis.

SOLUBLE IRON SALTS USEFUL AS CO-REACTANTS

In addition to the uronic acids and the strong base, the third raw material is a water soluble iron salt. The valence of the iron in the iron salt does not appear to be critical, and the relatively stable ferric or iron (III) salts such as ferric chloride are fully operative. It is preferred that the anion of the soluble iron salt not be a complexing agent or potential ligand for iron cations. These anions should also be pharmaceutically acceptable. To avoid hydrolysis of the iron salt starting material, it is preferred to first dissolve the solid salt in an aqueous acidic medium. At a pH below 7, ferric hydroxide is generally not formed and ferrous or ferric ions should stay in aqueous solution.

In addition to the ferric halides, other ferric salts of strong acids have good water solubility, including ferric acetate or nitrate and ferric sulfate nonahydrate. In addition, several water soluble ferrous salts are known and can be used in this invention, provided that the tendency of the ferrous ion to oxidize to the ferric state does not create significant storage or handling problems.

PROCESS OF MANUFACTURE

The substantially monomeric uronic acid starting material, as such or in neutralized (uronate) form, is blended with the water soluble iron salt in an acidic aqueous medium. (Alternatively, the reaction medium can be neutral or basic, provided that the soluble iron salt has been previously dissolved in an acidic aqueous medium which is then added to the reaction medium.) During this blending step, water-insoluble precipitates or suspensions can and typically do form. However, upon further adjustment of the pH to ensure the conversion of free carboxyls to carboxylate, these precipitates or suspensions can re-dissolve. When the neutralizing agent is sodium hydroxide or an alkaline sodium salt, redissolving of most insoluble materials appears to occur when a pH of at least 8 or 9 is reached (with agitation), and there appears to be no advantage in exceeding a pH of 10 or 11. The solubilizing of the product in an alkaline medium indicates that the iron is complexed, and substantially no ferric ion is available for the formation of ferric hydroxide.

The solubilized iron complex can be recovered by a variety of techniques including precipitation with polar, water-miscible organic solvents, evaporation, spray-drying, and the like. As mentioned previously, the preferred water-miscible solvents are the $C_1$-$C_3$ alkanols, particularly isopropyl alcohol. The iron complexes of this invention are sufficiently insoluble in isopropyl alcohol such that aqueous solutions of this alcohol can be added to the reaction medium for the purpose of precipitation of the reaction product. 50–99% (by weight or by volume) aqueous ispropyl alcohol can be used, optimum results being obtained with the 70% solution.

Iron mannuronate complexes can be obtained from mannuronates, which in turn can be obtained from alginic acid or alginates . See Example 10 of U.S. Pat. No. 3,901,874, which is incorporated herein by reference.

USES OF THE IRON COMPLEX

The iron complexes of the invention are useful as hematinics in the treatment or prevention of iron deficiency anemia in mammals. These hematinics can be administered orally or parenterally, the preferred route of administration being oral. Dosage units can be similar to ferrous sulfate and other known hematinics. The $LD_{50}$ values provide a sufficient safety factor, so that an oral dosage within the range of 10-500 milligrams for a 70 kilogram mammal is only a tiny fraction of the $LD_{50}$.

One particularly preferred use of the hematinics of this invention is in the field of animal feed or foodstuffs enrichment or supplementation. Unlike ferrous sulfate, the hematinics of this invention are compatible with a wide variety of materials which may be contained in foodstuffs or animal feeds, e.g. tannins, vegetable astringents, and the like. Furthermore, in the case of flour, cereals, and other starch-containing or carbohydrate-containing foodstuffs, the hematinics of this invention appear to have no adverse effect upon color. In the case of foodstuffs containing fats and oils, there appears to be little or no tendency to accelerate formation of rancid fat or oil degradation products. Other foodstuffs or edible or chewable materials in which the hematinics of this invention can be used for iron enrichment include alcoholic beverages (e.g. wine) in which the hematinic is dissolved and chewing gums, in which the hematinic can be dispersed. Effective amounts of hematinic can be used (e.g. 1–300 mg per serving or 10-500 mg per total daily consumption of foodstuff).

Similarly, these hematinics are compatible with a wide variety of liquid and solid pharmaceutical extending media, and suitable oral dosage units can be made into pills, capsules, tablets, and the like. Suitable multiples of the oral dosage unit can be made into syrups.

The following Examples illustrate the principle and practice of this invention without in any way limiting its scope.

EXAMPLE 1

An aqueous iron solution was prepared containing 0.2 mol per liter of ferric chloride and 0.1 mol per liter of hydrochloric acid. The latter serves to prevent hydrolysis of the ferric chloride in the aqueous solution. Also, 2.546 grams of galacturonic acid monohydrate (molecular weight 212.16, Eastman Organic Chemicals) were dissolved in 50 ml of distilled water. The galacturonic acid solution was neutralized by slowing adding — with good stirring — solid sodium carbonate monohydrate until pH test paper showed a pH of $9 \pm 1$. Great precision is not needed for this step. Next, 120 ml of the above iron solution (containing 3.892 grams of ferric chloride) were added slowly, with moderate stirring, to the above solution of galacturonic acid. The resultant very acid mixture was again neutralized by the addition of solid sodium carbonate monohydrate. At one point during this latter addition, the solution became very turbid with an insoluble iron salt of the iron-galacturonic acid complex, but this turbidity disappeared completely when a pH of about 9 was reached. At this point, the solution was of a very deep red-brown color, and it was perfectly clear. It was gently warmed on a hot plate to about 40° C. in order to expel the carbon dioxide formed in the neutralization process. The solution was then cooled to room temperature and added to 800 ml of isopropyl alcohol (aqueous, 70% by volume) with good stirring. A dark brown precipitate was then formed which settled readily to the bottom of the beaker upon cessation of the stirring. The supernatant liquid was substantially colorless. Precipitate and supernatant liquid were filtered off on a Buchner funnel. Filtration was rapid. The filter cake was washed three times with absolute isopropanol and dried. A dark, coffee-brown solid product was obtained which was loose and required no grinding. The size of the particles obtained was less than 200 mesh. Analysis by an independent academic laboratory showed the product to contain 29.5% iron and 7.6% sodium by weight. The product was easily soluble in water; the solution had a faint fruit flavor and was not astringent in low concentrations. The yield of solid product was 4.4 grams. The product was tested for hematinic activity; see Example 7.

EXAMPLE 2

2.546 grams of the same galacturonic acid described in Example 1 were dissolved in 50 ml of distilled water, and 120 ml of the same ferric chloride solution described in the preceding example were added thereto slowly, with stirring, by means of a pipette. The acid mixture was then neutralized slowly by the addition of an aqueous solution of sodium carbonate monohydrate containing approximately 30 grams of the salt per 100 ml of distilled water. Addition was made by dropping the soda solution into the acid mixture from a burette at the rate of approximately 1 drop per second, until a pH of $9 \pm 1$ was reached. Because of the greater dilution of the reactants in this example, compared with that in Example 1, the reaction mixture was added from a dropping funnel to a beaker containing 1,800 ml of a 70:30 isopropanol:water mixture. A very fine-grained dark brown-red precipitate was obtained which settled to the bottom of the beaker very readily, leaving a clear and colorless supernatant which contains no iron as proven by a thiocyanate test. Filtration with the procedure described in Example 1 was fast, and the yield of dry, chocolate-brown product was 4.3 grams. Analysis proved the product to contain 29.0% iron and 8.1% sodium. Animal tests for bioavailability of the iron in this product gave substantially the same results as reported in Example 7 for the product of Example 1.

Yields obtained in the two examples, the analyses of the two products, and the results of animal bioavailability tests leave no doubt that the two products are substantially identical, though the product of Example 2 seems to contain a very small amount of an impurity, most probably sodium chloride which is one of the products of reaction.

EXAMPLE 3

20 grams of a pure galacturonic acid were dissolved in 100 ml of distilled water. 54.06 grams of ferric chloride hexahydrate ($FeCl_3 \cdot 6\ H_2O$) were dissolved in 300 ml of distilled water. The two solutions were mixed thoroughly and then 48 grams of solid sodium carbonate monohydrate ($Na_2CO_3 \cdot 1\ H_2O$) were added slowly, with good stirring. The final solution had a pH of 9 to 10, was clear, and of dark brown-red color. To this solution there was added 280 ml of 99% isopropanol, slowly and with good stirring. A dark brown-red, fine-grained precipitate was obtained which was filtered off easily under suction.

EXAMPLE 4

25.5 grams of high-purity galacturonic acid were dissolved in 300 ml of distilled water with the addition of solid sodium carbonate until a pH of 8 to 9 was reached. Separately, 24 grams of anhydrous ferric chloride were dissolved in 300 ml of distilled water and this solution was then added slowly, by dropping funnel, to the aforementioned solution of galacturonic acid, adjusting with solid sodium carbonate as needed to keep the mixture slightly alkaline, e.g. pH 8–9, and keeping the mixture stirred moderately. A beautiful brown-red solution was thus obtained. In order to ascertain the maximum amount of iron which can be complexed with galacturonic acid, a solution of 189.9 grams of anhydrous ferric chloride was dissolved in 1500 ml of distilled water, and this solution was added gradually to the above solution, with good stirring, and always adjusting the alkalinity to a pH of 8–9. It was found that the resulting mixture remained clear and dark brown-red until about 270 ml of the latter ferric chloride solution has been added. A light-brown precipitate then appeared which, however, was dissolved again completely in about an hour's time and a perfectly clear, deep brown-red solution again resulted. From the total amounts of galacturonic acid used and ferric chloride solution consumed in the test, it was calculated that one mol weight of galacturonic acid will complex three atom weights of iron. Actually, 2,989 atom-weights of iron were consumed, an amount well within experimental error.

EXAMPLE 5

20 ml of the second ferric chloride solution used in Example 4 (the one containing 189.9 grams in 1500 ml of distilled water) were precipitated with 5% aqueous ammonia and washed by decantation with distilled water in order to remove the ammonium chloride formed in the reaction. The suspension was left standing for two days. Addition of solid galacturonic acid to this suspension does not dissolve the precipitate of ferric hydroxide to any considerable extent, and the addition of anhydrous sodium carbonate resulted in a very minimal amount brown-red color in the water. It was concluded that ferric hydroxide, though suspended in water, polymerized or otherwise changed on standing so that it no longer could dissolve in galacturonic acid or sodium galacturonate solution. On addition of sufficient hydrochloric acid, a clear, yellow solution resulted and, when anhydrous sodium carbonate was then added, the customary deep brown-red color of the iron-galacturonate complex developed. It was concluded that the "aging" of ferric hydroxide is detrimental in producing the iron complexes of the present invention.

EXAMPLE 6

The purpose of this Example is to demonstrate that galacturonic acid suitable for use in making hematinics of this invention can be obtained in a relatively straight-forward manner through the hydrolysis of pectin. Although mineral acids can be used for this purpose, the acid used in this Example is of the ABS (alkyl benzene sulfonic) type. A complete description of suitable ABS acids and procedures for using them is contained in U.S. Patent Application Ser. No. 417,553, filed Nov. 20, 1973, (William H. Hill), now U.S. Pat. No. 3,901,874, which is incorporated herein by reference.

Two grams of ABS acid SA-597 of Continental Oil Company were added dropwise to 4 grams of CAB-O-SIL H-5 (trademark of the Cabot Corporation for fumed or pyrogenic silica) in a 400 milliliter beaker and stirred well. Then 100 grams of Mutual Citrus Pectin, 220 grade, were added and stirred in until a generally uniform mixture was obtained. The mixture was placed in a ball mill and milled. The mill was opened and an additional 94 grams of the same pectin were added. The milling was continued. The mill was opened and the contents dumped onto a 20 mesh screen. 20 parts by weight of the above mixture were placed in a pressurized zone and heated at a temperature of 90° C. until substantially monomeric galacturonic acid was obtained. The resulting galacturonic acid was added to water and dissolved. Then an acidified ferric chloride solution was added to the water. Finally, very slowly, solid sodium carbonate monohydrate was added to the solution, resulting in a dark, red-brown solution which was centrifuged to yield a clear solution of much the same color along with very small amounts of cream-colored sediment as bottom pads in the centrifuge tubes. This sediment appeared to be residual "CAB-O-SIL" (fumed or pyrogenic silica) and was discarded. The clear, dark, red-brown supernatant contained the iron complex. This iron complex could be isolated with isopropyl alcohol precipitation in a manner described in the preceding Examples.

EXAMPLE 7

The following general procedure was used to make iron (III) glucuronolactone and iron(III) D-glucuronate.

A pre-weighed amount of the glucuronic acid or lactone was dissolved in water, and sodium carbonate was added to bring the pH of the solution to 10. The appropriate volume of ferric salt solution was added slowly. The addition was controlled so that the evolution of carbon dioxide from the resulting solution was very slow. A reddish solution resulted, which was slightly acidic. Sodium carbonate was added slowly with constant stirring until the evolution of carbon dioxide ceased. At approximate neutrality, a rusty colored suspension formed. Further addition of sodium carbonate cleared up the suspension and restored a clear solution by the time a pH of 10 was reached. This alkaline solution was dark brown and was warmed from about one hour. After cooling, the solution was poured into aqueous isopropyl alcohol with constant stirring. A fluffy precipitate would usually form; if precipitation did not occur, it could be brought about by slowly adding 100% anhydrous isopropyl alcohol. However, it was generally preferred to avoid adding so much isopropyl alcohol that the total alcohol content would reach 65%. At these high concentrations of alcohol, gummy materials may form. The mixture (containing the precipitate) is allowed to stand overnight before filtering. The precipitate was filtered by suction and washed first with 50% alcohol and then twice with 100% alcohol.

a. Iron(III) Glucuronolactone

The complexed-iron solution was yellowish-brown. Gummy material formed even with 50% alcohol. The gummy residue was air-dried for several days. It can then be recovered as a crystalline solid. The gummy residue was particularly likely to form with an Fe(III):lactone ratio of 1:3. With a ratio of 1:1, a higher percentage of alcohol can be tolerated. In the case of the 1:1 ratio, the precipitate was isolated from approximately 60% alcohol. The precipitate was a very dark brown, and 3.8 grams were obtained from 3.5 grams of lactone. A black-brown precipitate was obtained from an Fe(III):lactone ratio of 2:1 by pouring the iron complex-containing solution into 75% alcohol, resulting in an equilibrium composition of alcohol of about 57%. A precipitate was also obtained with a 3:1 Fe(III):lactone ratio.

b. Reaction Product of Ferric Salt and Alpha - D-glucuronic Acid

Precipitates were successfully obtained from 50–55% alcohol using the following Fe(III):glucuronic acid ratios:

1:1, 1:2, and 1:3

In the 1:2 synthesis, an equal volume of the aqueous iron complex mixture was added to 100% alcohol, and a gummy material formed. However, after draining the supernatant and dissolving the gummy material in a small amount of water, a fine precipitate was formed when adding this redissolved material to alcohol.

Precipitates tended to be greenish-brown.

EXAMPLE 8

This Example described a test comparing the bioavailability of iron in the iron complex of Example 1 with that of reagent grade ferrous sulfate (heptahydrate) for the anemic rat. Reagent grade ferrous sulfate heptahydrate (Fisher Scientific Co.) was used without further purification at the calculated iron content of 20.1%.

a. Experimental Method

Weanling male albino rats (Wistar-derived stock weighing between 45 and 55 grams) were placed in individual cages (newly galvanized) and provided with food and distilled water, ad libitum. The iron-low diet was that described by Pla and Fritz (J. Assoc. Offic. Anal. Chem. 54, 18 (1971). Weekly determination of hemoglobin content in tail blood was determined by the cyanomethemoglobin method of Drabkin adapted to 0.02 ml samples as recommended by these authors.

The iron reserves of the rats used depleted more slowly than those reported by Pla and Fritz so that stable hemoglobin values of about 8.3–8.5 g/100 ml were reached only after six weeks on the iron-low diet. 18 rats were selected for the test from a larger number to provide three matched groups of six, each having essentially equal initial hemoglobin values. These three groups are hereinafter referred to as the Example 1 (test) Group, the Ferrous Sulfate (Standard) Group and the Negative Control Group.

Based on the assumed iron content of both the hematinic (29.5%) and of the ferrous sulfate, aqueous solutions were prepared fresh each week day so that a uniform dose of 1 ml per rate would contain 0.2 mg of iron. The solution prepared on Fridays was also dosed on Saturdays and Sundays. The solutions were administered by intragastric intubation. The Negative Control Group received sham treatment consisting of plain water.

Body weights of all animals were recorded weekly and hemoglobin determinations were repeated after two and four weeks of dosing.

b. Results and Discussion

All animals were observed daily for any evidence of adverse effects which could be considered related to treatment. No such effects were seen. The rats behaved normally, had normal appetites, and showed no change in color or consistency of the fecal pellets.

The body weight gain for the Ferrous Sulfate Group averaged slightly better; as compared to the Example 1 Group; however, the differences were nominal. The Negative Control Group showed a significantly lower weight gain as compared to either the Example 1 Group or the Ferrous Sulfate Group.

The Example 1 Hematinic preparation was at least as available to the rat as the iron in ferrous sulfate with respect to bringing about repletion and hemoglobin production in partially anemic rats.

The Negative Control Group rats showed no average improvement in hemoglobin values in the 0–2 week period and slight improvement in the third and fourth weeks. Both the Ferrous Sulfate and Example 1 Groups showed significant improvement both after two weeks and after four weeks. On the average, the improvement was slightly greater in the Example 1 Group.

The colony stock from which these rats were drawn as weanlings (at 25 days of age) probably has somewhat higher iron reserves than those used by Pla and Fritz. Furthermore, since no use of tail-cups was made here, the inevitable coprophage of all rats acted to conserve iron present as body stores.

Nevertheless, it can be concluded that this test provided a valid demonstration of the efficacy of ferrous sulfate (i.e., the Standard) in reversing mild deficiency anemia and that the Example 1 hematinic was at least as effective as the Standard if not slightly more effective.

EXAMPLE 9

In a prophylatic test of the effectiveness of the hematinic of Example 1, the test used differed from JAOAC 54: 13-17 (1971) in that the rats were not depleted before they received the test diets. The Example 1 hematinic was found to range from 64–75% of the bioavailability of $FeSO_4$ heptahydrate, reagent grade and showed superior bioavailability as compared to reduced iron particles (95% of particles under 5 microns). These findings were based on observations of hemoglobin and hematocrit in the blood of the test animals and the Negative Control animals.

What is claimed is:

1. A composition containing bioavailable iron, said composition consisting essentially of the monomeric galacturonate or glucuronate reaction product of the components comprising:

b. about one, but no more than about four moles of a water soluble iron salt per equivalent of said component (a), wherein M is a pharmaceutically acceptable cation, and m is the valence of M.

2. A solid, water-soluble, 2-propanol insoluble composition consisting essentially of an iron complex which is the reaction product of essentially monomeric galacturonic acid or lactone thereof, a water soluble ferric salt, and sodium hydroxide or an alkaline sodium salt, said complex containing about 25–34% by weight of iron and about 7–9% by weight of sodium, said complex having, when tested in a curative oral administration test according to the cyanomethemoglobin method of Drabkin for hemoglobin determination, substantially 100% of the iron bioavailability of ferrous sulfate.

3. The complex of claim 1 combined with a pharmaceutically acceptable extender.

4. The composition of claim 2 combined with a pharmaceutically acceptable extender.

5. The complex of claim 21 wherein M is sodium and m is one.

6. The composition of claim 2 wherein said essentially monomeric galacturonic acid is obtained from the acid hydrolysis of polygalacturonic acid.

7. A foodstuff comprising a carbohydrate-containing or proteinaceous material blended with the complex of claim 1.

8. A foodstuff comprising a carbohydrate-containing or proteinaceous material blended with the composition of claim 2.

9. An alcoholic beverage comprising an effective amount of the complex of claim 1 dissolved therein.

10. A chewing gum product comprising an effective amount of the complex of claim 1 dispersed therein.

* * * * *

UNITED STATES PATENT AND TRADEMARK OFFICE
CERTIFICATE OF CORRECTION

PATENT NO. : 4,058,621
DATED : November 15, 1977
INVENTOR(S) : William W. Hill

It is certified that error appears in the above-identified patent and that said Letters Patent are hereby corrected as shown below:

In column 1, line 57, for "mammalina" read --mammalian--.
In column 4, line 11, for "literture" read --literature--.
In column 6, line 30, for "by by-products" read --with by-products--.
In column 11, line 3, for "has" read --had--.
In column 12, line 27, for "from" read --for--.
In column 13, line 9, for "described" read --describes--.
In column 13, line 41, for "rate" read --rat--.
In column 13, line 45, for "intubulation" read --intubation--.
In column 14, line 67, for "21" read --1--.

Signed and Sealed this

Nineteenth Day of September 1978

[SEAL]

Attest:

RUTH C. MASON
Attesting Officer

DONALD W. BANNER
Commissioner of Patents and Trademarks